United States Patent
Nord et al.

(10) Patent No.: US 11,364,393 B2
(45) Date of Patent: Jun. 21, 2022

(54) RADIATION TREATMENT PLANNING AND EXECUTION

(71) Applicant: Varian Medical Systems International AG, Cham (CH)

(72) Inventors: Janne I. Nord, Espoo (FI); Juha Kauppinen, Espoo (FI); Lasse H. Toimela, Helsinki (FI)

(73) Assignee: Varian Medical Systems International AG

(*) Notice: Subject to any disclaimer, the term of this patent is extended or adjusted under 35 U.S.C. 154(b) by 515 days.

(21) Appl. No.: 15/336,402

(22) Filed: Oct. 27, 2016

(65) Prior Publication Data
US 2018/0117358 A1    May 3, 2018

(51) Int. Cl.
*A61N 5/10* (2006.01)

(52) U.S. Cl.
CPC ......... *A61N 5/1037* (2013.01); *A61N 5/1031* (2013.01); *A61N 5/1036* (2013.01); *A61N 5/1045* (2013.01); *A61N 5/1049* (2013.01); *A61N 5/1067* (2013.01); *A61N 5/1068* (2013.01); *A61N 5/1081* (2013.01)

(58) Field of Classification Search
CPC .... A61N 5/103; A61N 5/1031; A61N 5/1037; A61N 5/1038; A61N 5/1042; A61N 5/1043; A61N 5/1045; A61N 5/1047; A61N 5/1068; A61N 5/1081; A61N 5/1082
See application file for complete search history.

(56) References Cited

U.S. PATENT DOCUMENTS

| 6,888,819 | B1 | 5/2005 | Graf |
| 7,283,611 | B1* | 10/2007 | Luan ............ A61N 5/103 378/51 |
| 7,649,981 | B2 | 1/2010 | Seppi et al. |
| 2004/0024300 | A1 | 2/2004 | Graf |

(Continued)

FOREIGN PATENT DOCUMENTS

WO    WO 2011160235 A1    12/2011

OTHER PUBLICATIONS

Pepin, Eric W., et al., "Dynamic gating window for compensation of baseline shift in respiratory-gated radiation therapy," Med. Phys. 38 (4), Apr. 2011, 7 pages.

(Continued)

*Primary Examiner* — Carrie R Dorna
(74) *Attorney, Agent, or Firm* — Vista IP Law Group, LLP

(57) ABSTRACT

An apparatus for use in a treatment planning process or in a treatment process, includes: an input for obtaining a parameter representing a number of beam on-off transitions; and a treatment planner configured to optimize a treatment plan based on parameter representing the number of beam on-off transitions. An apparatus includes: an input configured to obtain a width of a gating window for a treatment plan; and a gating window adjustor configured to adjust the width of the gating window during a treatment session. An apparatus includes: a dose calculator configured to calculate doses for different treatment variations; an evaluator configured to evaluate treatment acceptance criteria against the calculated doses; and a delivery limit module configured to determine one or more limits for one or more delivery parameters based on an evaluation of the treatment acceptance criteria by the evaluator.

33 Claims, 8 Drawing Sheets

(56) References Cited

U.S. PATENT DOCUMENTS

| | | |
|---|---|---|
| 2005/0084073 A1 | 4/2005 | Seppi et al. |
| 2008/0144772 A1* | 6/2008 | Yi .................... A61N 5/1049 378/65 |
| 2009/0116616 A1* | 5/2009 | Lu .................... A61N 5/1049 378/65 |
| 2010/0104068 A1 | 4/2010 | Kilby et al. |
| 2012/0083681 A1* | 4/2012 | Guckenburger ....... A61N 5/103 600/407 |
| 2013/0070898 A1* | 3/2013 | Stahl ................ A61N 5/1037 378/65 |
| 2015/0360051 A1 | 12/2015 | Martin et al. |

OTHER PUBLICATIONS

International Search Report for corresponding PCT Application No. PCT/IB2017/001305, 12 pages.

International Search Report and Written Opinion dated Apr. 13, 2018 for corresponding PCT Application No. PCT/IB2017/001305.

\* cited by examiner

RADIATION TREATMENT PLANNING AND EXECUTION

FIELD

This application relates generally to radiation therapy, and more specifically, to radiation treatment planning and execution.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes, in a radiation treatment procedure, a plurality of treatment sessions may be performed. In each treatment session, a radiation source may be placed at a prescribed gantry angle to thereby deliver radiation beam towards a target tissue from a certain angle. As a result of delivering radiation towards the target tissue from a plurality of different angles, a sufficient radiation dose may be delivered to the target tissue to thereby treat the target tissue, while surrounding healthy tissue may be protected.

Before a treatment procedure is performed, a treatment plan may first be determined. Methods and apparatuses for determining treatment plan(s) are described herein.

SUMMARY

An apparatus for use in a treatment planning process or in a treatment process, includes: an input for obtaining a parameter representing a number of beam on-off transitions; and a treatment planner configured to optimize a treatment plan based on parameter representing the number of beam on-off transitions.

Optionally, the beam on-off transitions comprise a transition from beam-on to beam-off, a transition from beam-off to beam-on, or both.

Optionally, the treatment planner is configured to optimize the treatment plan to reduce the number of beam on-off transitions.

Optionally, the treatment planner is configured to optimize the treatment plan during the treatment planning process.

Optionally, the treatment planner is configured to optimize the treatment plan during the treatment process.

Optionally, the apparatus further includes a gating window adjustor configured to adjust a width of a gating window for the treatment plan.

Optionally, the gating window adjustor is configured to adjust the width of the gating window during a treatment session.

Optionally, the apparatus further includes a motion data analyzer configured to analyze motion data associated with a target, wherein the gating window adjustor is configured to adjust the width of the gating window based on a result from the act of analyzing.

Optionally, the apparatus further includes a treatment progress monitor configured to determine a status parameter indicating a treatment progress, wherein the gating window adjustor is configured to adjust the width of the gating window based on the status parameter.

Optionally, the apparatus further includes a treatment duration estimator configured to determine an expected treatment duration based at least in part on a planned monitor unit and the width of the gating window.

Optionally, the apparatus further includes a delivery limit module configured to determine a limit for a delivery parameter based on a treatment acceptance criterion.

Optionally, the delivery parameter comprises an isocenter position, a leaf position, a gantry angle, a collimator angle, a dose rate, a number of monitoring units, or any combination of the foregoing.

Optionally, the delivery limit module is configured to determine the limit automatically.

Optionally, the apparatus further includes: a dose calculator configured to calculate doses for different treatment variations; and an evaluator configured to evaluate treatment acceptance criteria against the calculated doses, the treatment acceptance criteria including the treatment acceptance criterion; wherein the delivery limit module is configured to determine the limit for the delivery parameter based on an evaluation of the treatment acceptance criteria by the evaluator.

A method for use in a treatment planning process or in a treatment process, includes: obtaining, by an input, a parameter representing a number of beam on-off transitions; and optimizing, using a treatment planner, a treatment plan based on parameter representing the number of beam on-off transitions.

Optionally, the beam on-off transitions comprise a transition from beam-on to beam-off, a transition from beam-off to beam-on, or both.

Optionally, the treatment plan is optimized to reduce the number of beam on-off transitions.

Optionally, the act of optimizing is performed during the treatment planning process.

Optionally, the act of optimizing is performed during the treatment process.

Optionally, the method further includes adjusting a width of a gating window for the treatment plan.

Optionally, the act of adjusting the width of the gating window is performed during a treatment session.

Optionally, the method further includes analyzing motion data associated with a target, wherein the act of adjusting the width of the gating window is performed based on a result from the act of analyzing.

Optionally, the method further includes determining a status parameter indicating a treatment progress, wherein the act of adjusting the width of the gating window is performed based on the status parameter.

Optionally, the method further includes determining an expected treatment duration based at least in part on a planned monitor unit and the width of the gating window.

Optionally, the method further includes determining a limit for a delivery parameter based on a treatment acceptance criterion.

Optionally, the delivery parameter comprises an isocenter position, a leaf position, a gantry angle, a collimator angle, a dose rate, a number of monitoring units, or any combination of the foregoing.

Optionally, the act of determining the limit is performed automatically by a delivery limit module.

Optionally, the method further includes: calculating doses for different treatment variations; and evaluating treatment acceptance criteria against the calculated doses, the treatment acceptance criteria including the treatment acceptance criterion; wherein the limit for the delivery parameter is determined based on a result from the act of evaluating the treatment acceptance criteria.

An apparatus for use in a treatment planning process or in a treatment process, includes: an input configured to obtain a width of a gating window for a treatment plan; and a gating window adjustor configured to adjust the width of the gating window during a treatment session.

Optionally, the apparatus further includes a motion data analyzer configured to analyze motion data associated with a target, wherein the gating window adjustor is configured to adjust the width of the gating window based on an output from the motion data analyzer.

Optionally, the output indicates a decrease in motion amplitude, and the gating window adjustor is configured to reduce the width of the gating window in correspondence with the decrease in the motion amplitude.

Optionally, the output indicates an increase in motion amplitude, and the gating window adjustor is configured to increase the width of the gating window in correspondence with the increase in the motion amplitude.

Optionally, the apparatus further includes a treatment progress monitor configured to determine a status parameter indicating a treatment progress, wherein gating window adjustor is configured to adjust the width of the gating window based on the status parameter.

Optionally, the status parameter indicates that the treatment progress is faster than a threshold, and the gating window adjustor is configured to reduce the width of the gating window in correspondence with the faster treatment progress.

Optionally, the status parameter indicates that the treatment progress is slower than a threshold, and the gating window adjustor is configured to increase the width of the gating window in correspondence with the slower treatment progress.

Optionally, the apparatus further includes a treatment duration estimator configured to determine an expected treatment duration based at least in part on a planned monitor unit and the width of the gating window.

A method for use in a treatment planning process or in a treatment process, includes: obtaining, by an input, a width of a gating window for a treatment plan; and adjusting, using a gating window adjustor, the width of the gating window during a treatment session.

Optionally, the method further includes analyzing motion data associated with a target, wherein the act of adjusting the width of the gating window is performed based on a result from the act of analyzing.

Optionally, the result from the act of analyzing indicates a decrease in motion amplitude, and the width of the gating window is reduced in correspondence with the decrease in the motion amplitude.

Optionally, the result from the act of analyzing indicates an increase in motion amplitude, and the width of the gating window is increased in correspondence with the increase in the motion amplitude.

Optionally, the method further includes determining a status parameter indicating a treatment progress, wherein the act of adjusting the width of the gating window is performed based on the status parameter.

Optionally, the status parameter indicates that the treatment progress is faster than a threshold, and the width of the gating window is reduced in correspondence with the faster treatment progress.

Optionally, the status parameter indicates that the treatment progress is slower than a threshold, and the width of the gating window is increased in correspondence with the slower treatment progress.

Optionally, the method further includes determining an expected treatment duration based at least in part on a planned monitor unit and the width of the gating window.

An apparatus for use in a treatment planning process or in a treatment process, includes: a dose calculator configured to calculate doses for different treatment variations; an evaluator configured to evaluate treatment acceptance criteria against the calculated doses; and a delivery limit module configured to determine one or more limits for one or more delivery parameters based on an evaluation of the treatment acceptance criteria by the evaluator.

Optionally, the delivery parameter comprises an isocenter position, a leaf position, a gantry angle, a collimator angle, a dose rate, a number of monitoring units, or any combination of the foregoing.

Optionally, the delivery limit module is configured to determine the one or more limits automatically.

Optionally, the treatment acceptance criterion comprises a DVH criterion.

A method for use in a treatment planning process or in a treatment process, includes: calculating, by a dose calculator, doses for different treatment variations; evaluating, by an evaluator, treatment acceptance criteria against the calculated doses; and determining, by a delivery limit module, one or more limits for one or more delivery parameters based on a result from the act of evaluating the treatment acceptance criteria.

Optionally, the delivery parameter comprises an isocenter position, a leaf position, a gantry angle, a collimator angle, a dose rate, a number of monitoring units, or any combination of the foregoing.

Optionally, the act of determining the one or more limits is performed automatically by the delivery limit module.

Optionally, the treatment acceptance criterion comprises a DVH criterion.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
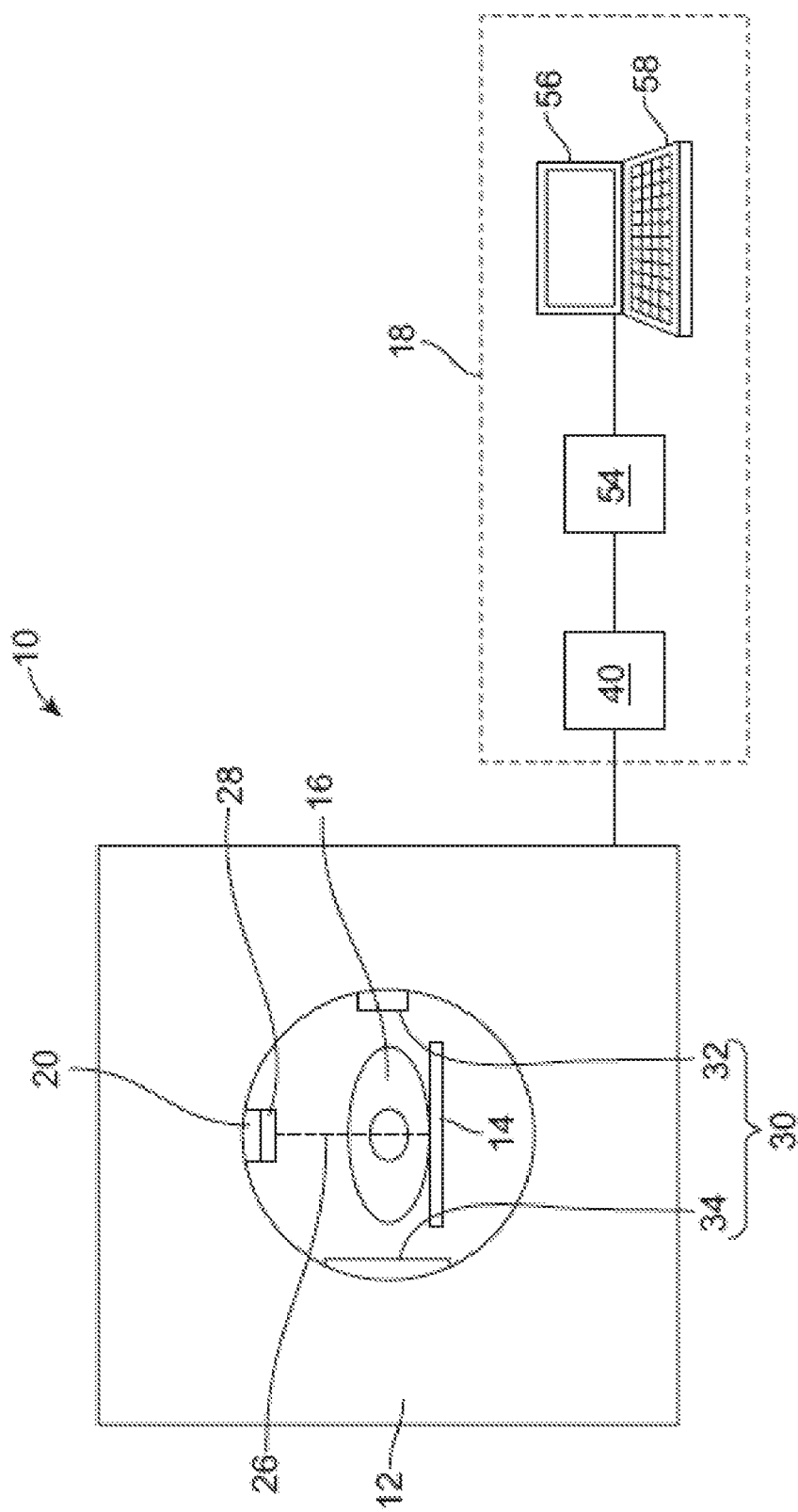
FIG. 1 illustrates a system for delivering radiation in accordance with a treatment plan determined in accordance with embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation treatment system 10 for delivering radiation in accordance with a treatment plan that is determined using techniques described herein. The system 10 includes a gantry 12, a patient support 14 for supporting a patient 16, and a control system 18 for controlling an operation of the gantry 12. The system 10 also includes a radiation source 20 that projects a beam 26 of radiation towards a patient 16 while the patient 16 is supported on support 14, and a collimator system 28 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In further embodiments, the radiation source 20 can be a diagnostic radiation source. In the illustrated embodiments, the radiation source 20 is rotatably coupled to the gantry 12. The radiation source 20 may be located within a bore (like that shown in the figure), or may be coupled to an arm.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rotate about the patient 16 during a treatment procedure. In such case, the gantry 12 may be fixed, and the patient support 14 is rotatable. The operation of the radiation source 20, the collimator system 28, and the gantry 12 (if the gantry 12 is rotatable), are controlled by the control 40, which provides power and timing signals to the radiation source 20 and the collimator system 28, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 16 completely through a 360° range, or partially through a range that is less than 360°. Also, in other embodiments, the radiation source 20 is translatable relative to the patient 16. In further embodiments, the source 20 may be coupled to the gantry 12 via an arm, in which case, the source 20 is located outside the bore of the gantry 12.

In some cases, the system 10 may optionally include one or more imaging devices. For example, as shown in FIG. 1, the system 10 may further include a x-ray source 32 and an imager 34 located opposite from the x-ray source 32. The x-ray source 32 and the imager 34 may be configured to image the patient 16 before a delivery of treatment energy (e.g., for patient setup), and/or during a treatment energy delivery session (e.g., between deliveries of radiation beams).

Although the above embodiments have been described with reference to delivering treatment radiation that is in the form of x-rays, in other embodiments, the system and technique described herein may be used for other types of treatment energy. For examples, in other embodiments, the radiation source 20 may be a proton source for delivering protons to treat a patient, an electron source for delivering electrons, or other types of particle source for delivering other types of particles for treating patient. Accordingly, embodiments of the treatment planning technique described herein may be used to determine treatment plan for other types of treatment, such as proton treatment, which may be considered to be a type of radiation treatment. Also, it should be noted that the term "collimator" is not limited to a device having leaves for blocking radiation, and may refer to a device having one or more jaws or jaw blocks. Thus, a position of a collimator may refer to position of leaves of a collimator, position of collimator jaws, or a global position of the collimator itself relative to some coordinate system (e.g., a position of the collimator relative to a gantry or relative to a radiation machine, etc.).

Figure 2:
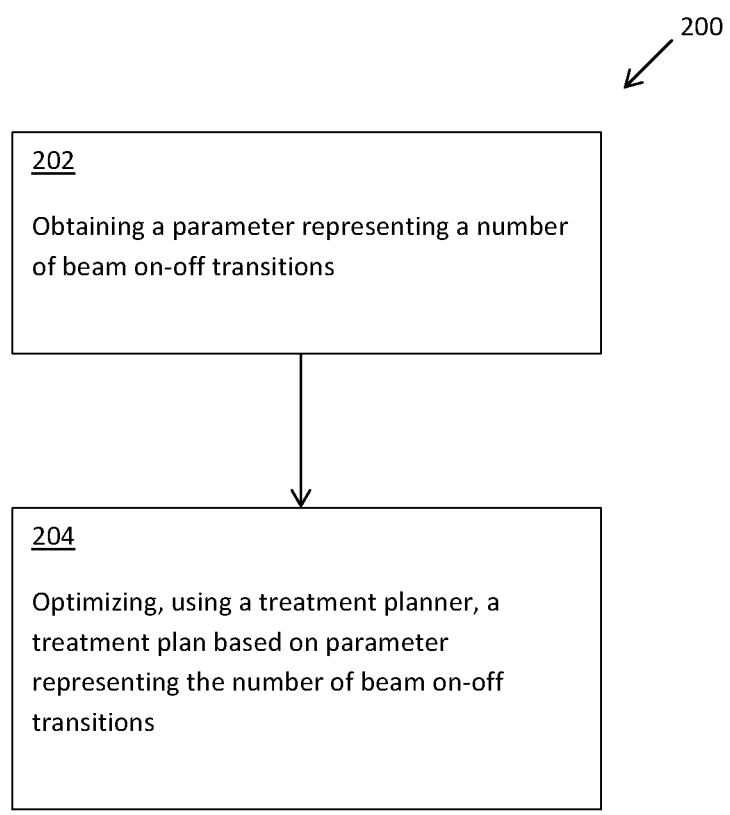
FIG. 2 illustrates a method for determining a treatment plan in accordance with some embodiments.

A method 200 for use in a treatment planning process or in a treatment process will now be described with reference to FIG. 2. The treatment plan may be used by the system 10 of FIG. 1 in some embodiments, but may also be used by other systems in other embodiments. First, the method 200 includes obtaining, by an input, a parameter representing a number of beam on-off transitions (item 202). The input may be an input generated by a processing unit, or it may be a user input provided by a user. The method 200 also includes optimizing, using a treatment planner, a treatment plan based on parameter representing the number of beam on-off transitions (item 204).

In some embodiments, the beam on-off transitions may include a transition from beam-on to beam-off, a transition from beam-off to beam-on, or both. The beam may be a treatment beam, such as a radiation beam generated using the system 10 of FIG. 1.

In some embodiments, the treatment plan may be optimized to reduce the number of beam on-off transitions. Reducing the number of beam on-off transitions (and possibly treat continuously with continuous beam) is advantageous because it may prevent or at least delay machine wear. In particular, reducing the number of beam on-off transitions will result in smaller number of machine ramp-ups, and the treatment machine will be worn less.

In some embodiments, the treatment planner may be configured to determine a treatment plan that provides gating. Gating may be used to improve accuracy of delivery of radiation dose when treating moving target (such as a target that moves due to a patient's breathing). The region where the treatment beam is turned on (gating window) may affect a duty cycle of treatment, which is fraction of time the beam is on. The region where the treatment beam is turned on may also affect an accuracy of the treatment. For example, smaller gating windows may produce more accurate dose delivery. In some embodiments, the treatment plan may be determined by optimizing the gating window to maximize the duty cycle. The treatment plan may also be determined by considering both the number of beam on-off transitions, as well as the gating window. For example, the duty cycle may be optimal when the gating window is positioned roughly in the middle of a sinusoidal motion (e.g., a respiratory cycle representation). However, that position of the gating window may result in a number of beam on-off transitions that is not optimal, because the beam is turned off twice in each cycle. If the gating window is positioned in either end of the periodic motion, then the beam may be turned off only once in each cycle. Thus, the gating window may be optimized so that beam holds are minimized (first priority), and duty cycle is maximized (second priority). In other embodiments, the duty cycle may be the first priority and the number of beam on-off transitions may be the second priority, when performing optimization to determine the treatment plan.

Also, in some embodiments, the treatment plan may be used in an arc treatment. In such cases, reducing the number of beam on-off transitions is also advantageous because it allows the gantry to rotate relatively more smoothly (compared to a treatment plan in which the beam on-off transitions is not optimized). Reducing the number of beam on-off transitions may also reduce treatment time.

In some embodiments, the act of optimizing may be performed during the treatment planning process. In other embodiments, the act of optimizing is performed during the treatment process.

Figure 3:
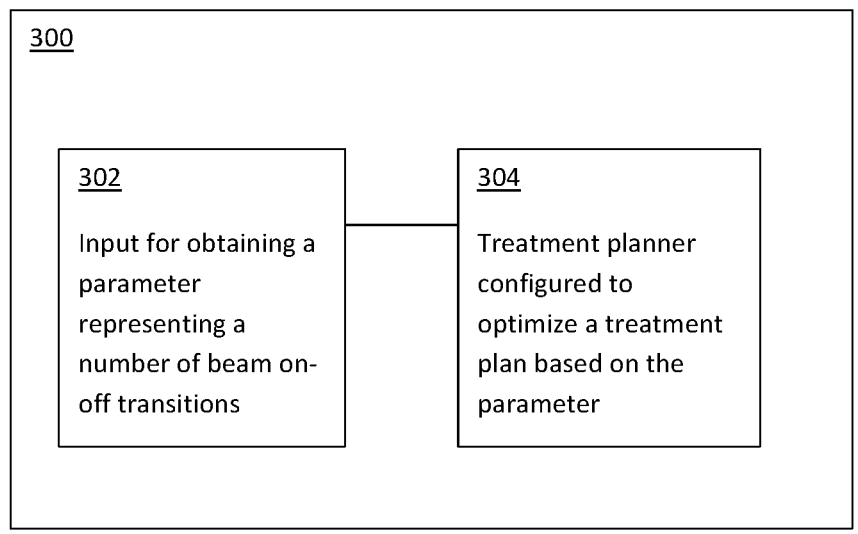
FIG. 3 illustrates an apparatus in accordance with some embodiments.

FIG. 3 illustrates an apparatus 300 that may be used to perform the method 200. The apparatus 300 is for use in a treatment planning process or in a treatment process. The apparatus 300 includes an input 302 for obtaining a parameter representing a number of beam on-off transitions. The apparatus 300 also includes a treatment planner 304 configured to optimize a treatment plan based on the parameter representing the number of beam on-off transitions.

In some embodiments, the treatment planner 304 is configured to optimize the treatment plan to reduce the number of beam on-off transitions.

In some embodiments, the treatment planner 304 is configured to optimize the treatment plan during the treatment planning process. In other embodiments, the treatment planner 304 is configured to optimize the treatment plan during the treatment process.

Figure 4:
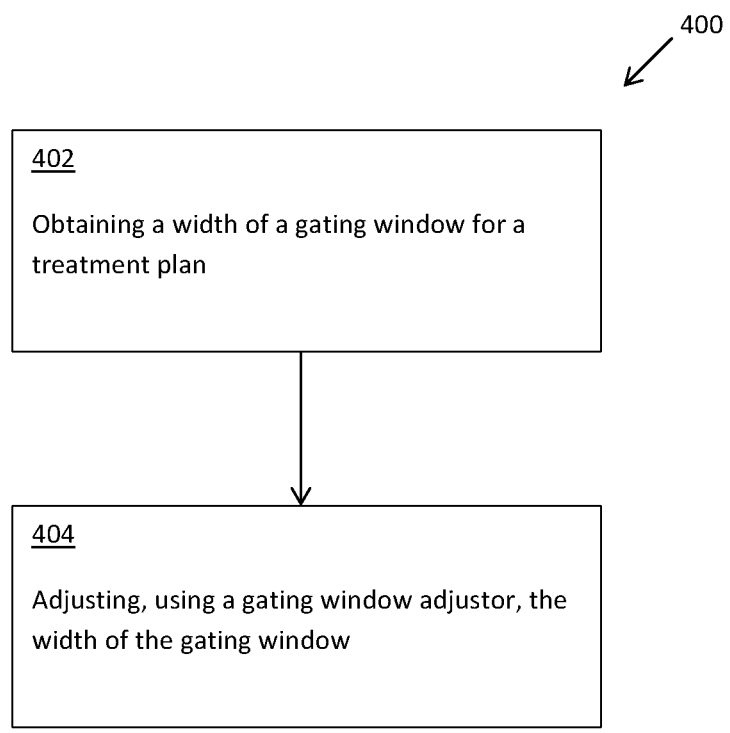
FIG. 4 illustrates a method for determining a treatment plan in accordance with some embodiments.

A method 400 for use in a treatment planning process or in a treatment process will now be described with reference to FIG. 4. The treatment plan may be used by the system 10 of FIG. 1 in some embodiments, but may also be used by other systems in other embodiments. First, the method 400 includes obtaining, by an input, a width of a gating window for a treatment plan (item 402). The method 400 also includes adjusting, using a gating window adjustor, the width of the gating window (item 404).

In some embodiments, the gating window adjustor may adjust the width of the gating window during a treatment session. In other embodiments, the gating window adjustor may adjust the width of the gating window during treatment planning.

Gating may be used in radiation therapy to pause radiation delivery if a radiation target has moved outside a predefined spatial region (e.g., that corresponds with a gating window). In some embodiments, the gating window may be initially predefined. During treatment, motion of target is analyzed. The motion of the target may be obtained from motion signal of a surrogate that moves in correspondence with the target. For example, the surrogate may be one or more markers coupled to a patient's chest. In such cases, as the patient breathes, the marker(s) will move up and down in correspondence with the patient's breathing. In other embodiments, the motion of the target may be obtained directly from images of the internal bodily structure of the patient. If the motion amplitude has decreased (e.g., compared to that of a reference motion), the gating window size may be reduced to improve dosimetric accuracy without deviating from the initial expected treatment delivery time. Reduction of gating window size means that the allowed range of spatial location of the tumor is smaller. Reduction of gating window size leads to 1) less variation in target locations during dose delivery and therefore more conformal dose distribution and 2) increase in delivery time. However, because the observed movement is smaller, even the smaller gating window leads to acceptable delivery time. On the other hand, if the motion amplitude has increased, the gating window size may be enlarged. In some embodiments, a maximum allowable width may be predefined for the gating window. In such cases, the gating window may be enlarged, but only to the extent of the predefined maximum allowable width.

Various techniques may be employed to determine how much to adjust the gating window. In some cases, beam-on time of treatment may be predetermined based on dosimetric planning. The total delivery time (wall-clock time) is a sum of passed delivery time and estimated remaining delivery time: $T_{tot}=T_{passed}+T_{estimate}$. These times include both beam-on and beam-off time. A goal delivery time may be defined in advance: $T_{goal}$. It may be chosen based on treatment time slot (allocated time for whole treatment including, for example, patient set-up). Some patients may not be able to be in treatment position for a long period of time, which may also affect decision of goal delivery time. Also, for shorter time periods, less motion or changes in patient (e.g., due to bladder movement, coughing, vomiting) are expected. The goal is to choose a gating window so that $T_{tot} \sim T_{goal}$. $T_{passed}$ can be determined using a clock or timer. The gating window may then be chosen so that if the motion continues as observed, the $T_{estimate}=T_{goal}-T_{passed}$. In some cases, a maximum size of gating window may be prescribed. In such cases, if the system determines a gating window larger than the maximum size is needed in order to meet $T_{goal}$, the maximum size is used and $T_{goal}$ may be exceeded.

In one example, the movement of the patent may be observed (e.g., using one or more cameras, or any of other position measuring devices), and the positional data may be binned to 4 different groups or bins: 1, 2, 3 and 4. In this example, it is assumed that the allowed maximum range for gating window is at positions 2, 3, 4 (which may be determined during an initial treatment planning). Also, in this example, it is assumed that goal treatment time $T_{goal}$ is 60 seconds, and the planned beam-on time is 30 seconds. The observed distribution of positions in the beginning may be, for example:

Position 1: 1 sample
Position 2: 1 sample
Position 3: 1 sample
Position 4: 1 sample.

In this example, each of the positions 1-4 may be a range of positions. For example, position 1 may represent positional range of 0 cm to 1 cm, position 2 may represent positional range of 1 cm to 2 cm, position 3 may represent positional range of 2 cm to 3 cm, and position 4 may represent positional range of 3 cm to 4 cm. Also, in the above example, a "sample" refers to observation of target (e.g., tumor) position. In the above example, the target is observed once in each of the four positions 1-4. Assuming positions 3 and 4 are for beam-on in the initial treatment plan. This produces an estimated delivery time of 60 seconds, which is also the goal delivery time.

After 30 seconds, the distribution may change so that (during one cyclical motion), for example:

Position 1: 0 sample
Position 2: 1 sample
Position 3: 1 sample
Position 4: 2 samples.

That means the target is observed once to be in position 2, once to be in position 3, and twice to be in position 4.

Now assuming 15 seconds of the beam-on time has already been delivered, and 30 seconds of wall-clock time has passed. Therefore, $T_{passed}=30$ seconds. There is still a remaining of 15 seconds of the original 30 seconds of beam-on time to deliver treatment, and a remaining of 30 seconds of the original 60 seconds of the goal treatment wall-clock time to perform the treatment delivery. If the gating window is remained at positions 3 and 4, the estimated remaining time ($T_{estimate}$) would be 15 s*(1+1+2)/(1+2)=20 s, and total time $T_{tot}$=20 s+30 s=50 seconds. This is shorted than $T_{goal}$=60 seconds. On the other hand, by changing the gating window to position 4 only, the estimated remaining time would be $T_{estimate}$=15*(1+1+2)/(2)=30 s. The total time would be $T_{tot}=T_{estimate}$ $T_{passed}$=30 s+30 s=60 seconds. This is not larger than the goal treatment time. Accordingly, the gating window may be changed to position 4 only.

As another example, assuming the distribution after 30 seconds is:

Position 1: 3 samples
Position 2: 1 sample

Position 3: 1 sample
Position 4: 1 sample, the gating window may then be enlarged to position 2, 3, and 4. In such cases, $T_{estimate}$=15*(3+1+1+1)/(1+1+1)=30 s. The total time would be $T_{tot}=T_{estimate}+T_{passed}$=30 s+30 s=60 seconds. Thus, the 30 seconds of the estimated remaining beam-on time is reached, and the 60 seconds of total goal time is also reached.

Accordingly, in some embodiments, the method 400 may further include analyzing motion data associated with a target, wherein the act of adjusting the width of the gating window (item 4040) is performed based on a result from the act of analyzing. In some cases, the result from the act of analyzing indicates a decrease in motion amplitude, and the width of the gating window may then be reduced in correspondence with the decrease in the motion amplitude. In other cases, the result from the act of analyzing indicates an increase in motion amplitude, and the width of the gating window may be increased in correspondence with the increase in the motion amplitude.

In other embodiments, the gating window width may be adjusted based on a treatment progress. For example, a status parameter may be used to represent a treatment progress. In such cases, the width of the gating window may be adjusted based on the status parameter. Accordingly, in other embodiments, the method 400 may further include determining a status parameter indicating a treatment progress, wherein the act of adjusting the width of the gating window (item 404) is performed based on the status parameter. In some cases, the status parameter indicates that the treatment progress is faster than a threshold, and the width of the gating window may be reduced in correspondence with the faster treatment progress. The reduction in the width of the gating window may be performed to improve accuracy of the energy delivery without exceeding the desired treatment time (e.g., the treatment progress threshold). In other cases, the status parameter indicates that the treatment progress is slower than a threshold, and the width of the gating window may be increased in correspondence with the slower treatment progress to compensate for the slowness of the treatment progress.

Various techniques may be employed to determine the threshold for comparison with the treatment progress. In one technique, based on planned monitor units, analyzed gating signal and the initially predefined gating window, an estimated treatment time is computed, which will be used as a reference treatment time (threshold) for comparison. Alternatively, a user may input a maximum duration of treatment as the reference treatment time for use as a threshold for comparison with the actual treatment progress. Accordingly, in some embodiments, the method 400 may further include determining an expected treatment duration based at least in part on a planned monitor unit and the width of the gating window. The expected treatment duration may be determined by a treatment duration calculator in some embodiments. Also, in some embodiments, the expected treatment duration may be stored in a non-transitory medium for future processing, and/or may be displayed in a screen for presentation to a user.

Figure 5:
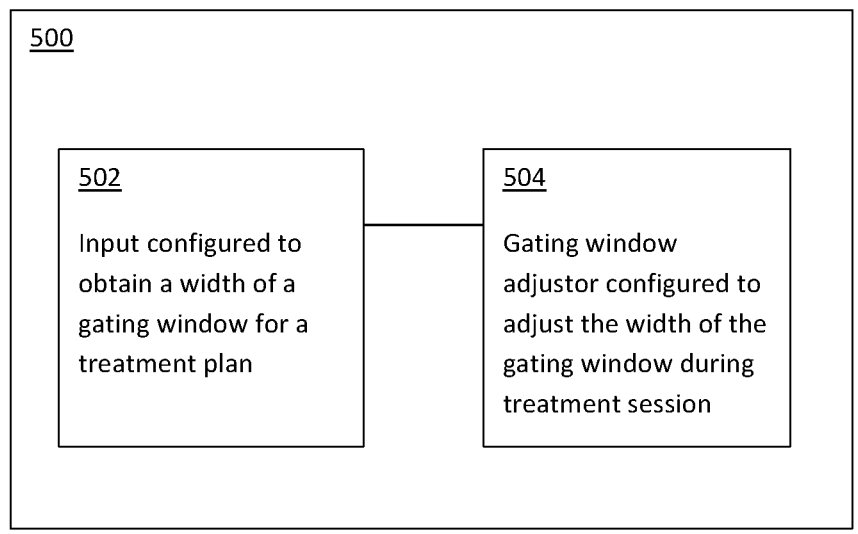
FIG. 5 illustrates an apparatus in accordance with some embodiments.

FIG. 5 illustrates an apparatus 500 that may be used to perform the method 400. The apparatus 500 is for use in a treatment planning process or in a treatment process. The apparatus 500 includes an input 502 configured to obtain a width of a gating window for a treatment plan. The apparatus 500 also includes a gating window adjustor 504 configured to adjust the width of the gating window during a treatment session.

In some embodiments, the apparatus 500 further includes a motion data analyzer configured to analyze motion data associated with a target, wherein the gating window adjustor 504 is configured to adjust the width of the gating window based on an output from the motion data analyzer. In some cases, the output indicates a decrease in motion amplitude, and the gating window adjustor 504 is configured to reduce the width of the gating window in correspondence with the decrease in the motion amplitude. In other cases, the output indicates an increase in motion amplitude, and the gating window adjustor 504 is configured to increase the width of the gating window in correspondence with the increase in the motion amplitude.

Also, in some embodiments, the apparatus 500 further includes a treatment progress monitor configured to determine a status parameter indicating a treatment progress, wherein gating window adjustor 504 is configured to adjust the width of the gating window based on the status parameter. In some cases, the status parameter indicates that the treatment progress is faster than a threshold, and the gating window adjustor 504 is configured to reduce the width of the gating window in correspondence with the faster treatment progress. In other cases, the status parameter indicates that the treatment progress is slower than a threshold, and the gating window adjustor 504 is configured to increase the width of the gating window in correspondence with the slower treatment progress.

In some embodiments, the apparatus 500 further includes a treatment duration estimator configured to determine an expected treatment duration based at least in part on a planned monitor unit and the width of the gating window.

Figure 6:
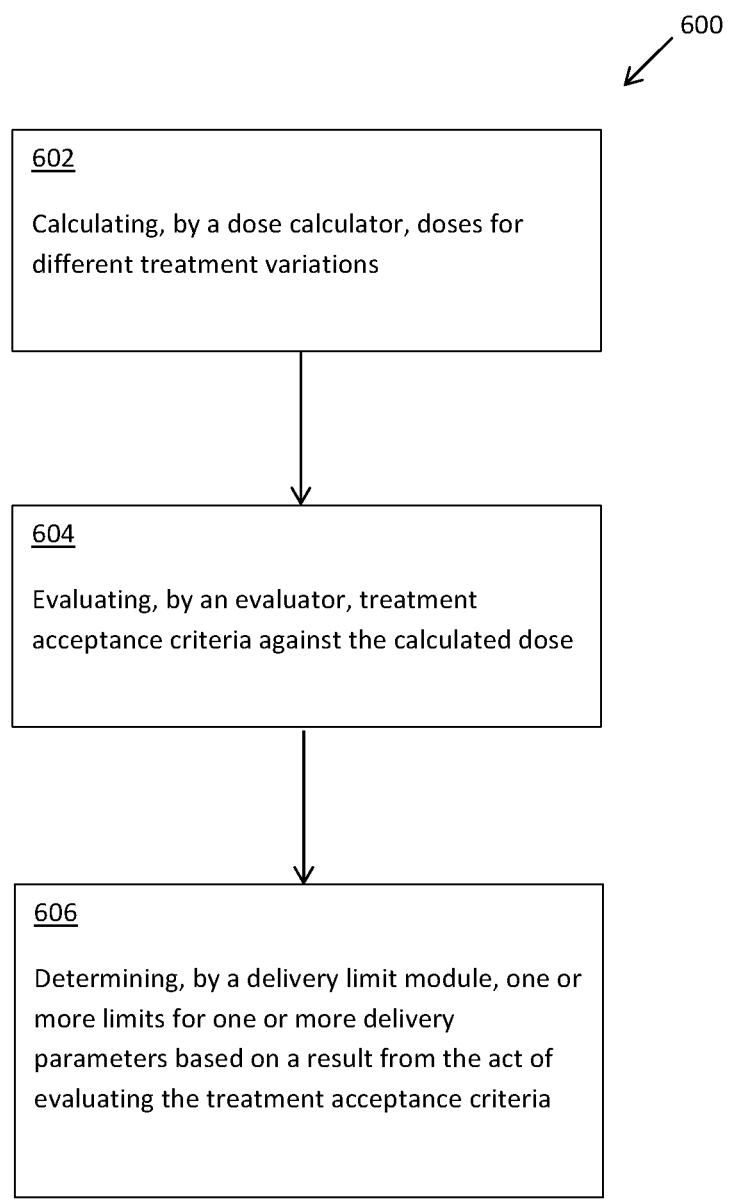
FIG. 6 illustrates a method for determining a treatment plan in accordance with some embodiments.

A method 600 for use in a treatment planning process or in a treatment process will now be described with reference to FIG. 6. The treatment plan may be used by the system 10 of FIG. 1 in some embodiments, but may also be used by other systems in other embodiments. First, the method 600 includes calculating, by a dose calculator, doses for different treatment variations (item 602).

The method 600 also includes evaluating, by an evaluator, treatment acceptance criteria against the calculated doses (item 604). In some cases, the treatment acceptance criterion may comprise a DVH criterion. For example, the DVH criterion may be: at most 20% of lung can receive a maximum of 20 Gy, at least 99% of target must receive at least 60 Gy, etc. In some embodiments, the acceptance criterion may be different from an optimization criterion for treatment plan determination (e.g., an optimization criterion for use in an optimization process to determine a treatment plan). For example, the acceptance criterion may be a treatment delivery time constraint, which may not be considered during optimization to determine a treatment plan. In other embodiments, the acceptance criterion may be the same as an optimization criterion. In other examples, the treatment acceptance criteria may comprise maximum point dose criteria, mean dose criteria, minimum dose criteria for tumorous tissue, conformity criteria, or any combination of the foregoing.

The method 600 further includes determining, by a delivery limit module, one or more limits for one or more delivery parameters based on a result from the act of evaluating the treatment acceptance criteria (item 606). By means of non-limiting examples, the one or more delivery parameters may comprise an isocenter position, a leaf position, a gantry angle, a collimator angle, a dose rate, a number of monitoring units, or any combination of the foregoing.

As an example of how items 602, 604, 606 are performed, consider the example of a tumor near a heart. The tumor is moving and strategy of moving isocenter within patient to track the tumor motion is selected as a movement compensation strategy. The isocenter movement to track the tumor motion may be performed by moving patient, by moving radiation source, or both. First a plan is generated for observed geometric conditions where the spatial separation between heart and tumor is longest. The isocenter is placed at the tumor to track the tumor. Tumor movement is imaged and 10 potential locations for tumor are identified from different potential treatment variations. According to movement compensation strategy, the isocenter would track the tumor and the corresponding isocenter locations are P1 to P10 for the 10 potential locations for the tumor. The dose is then calculated for each isocenter location. The calculated maximum doses for heart are, for example:

P1: 0.5 Gy
P2: 0.6 Gy
P3: 0.8 Gy
P4: 0.9 Gy
P5: 1.0 Gy
P6: 6.0 Gy
P7: 10.0 Gy
P8: 20.0 Gy
P9: 30.0 Gy
P10: 35.0 Gy.

In this case, assuming the physician accepts maximum 5 Gy as the maximum dose to heart. In the example, locations P1 to P5 pass the acceptance criteria and location P6 to P10 do not pass the acceptance criteria. Therefore the allowed isocenter range is allowed to cover tumor positions from P1 to P5.

In the above example, the isocenter locations may be, for example:

P1: 0.0 cm
P2: 0.1 cm
P3: 0.2 cm
P4: 0.3 cm
P5: 0.4 cm
P6: 0.6 cm
P7: 0.7 cm
P8: 0.9 cm
P9: 1.0 cm
P10: 1.1 cm

Since P1-P5 are selected because they pass acceptance criteria, the corresponding allowed range of positions for the isocenter is 0.0 cm-0.4 cm.

The method 600 is advantageous because the delivery limits may be determined based on treatment acceptance criteria. Doses may be calculated automatically for different variations, and the acceptance criteria may be evaluated against the doses. The acceptable variations may then be used to generate limits for treatment delivery parameters. This technique is more efficient and less labor intensive compared to a solution in which limits are set manually by calculating doses with different variations of delivery parameters, and a clinical expert then choose the allowed limits. Also, in some cases, delivery parameters may need to be changed for a treatment delivery (e.g., due to moving target). Such may be done real time during delivery, and/or before treatment is delivered (e.g., while patient is on the patient support). The method 600 allows the limits of the changes for the delivery parameters to be changed during treatment delivery. Such may be done in real time during treatment delivery, before treatment is delivered while patient is on the patient support, and/or during treatment planning.

In some cases, the method 600 may optionally further include reducing the set of accepted variations. For example, all changes within 3 cm from original isocenter position may be considered as passing acceptance criteria, and changes over 3 cm may be considered unacceptable. Using the technique described herein, the reduced set of accepted variations may allow, for example, changes of less than 2.5 cm to ensure that small variation in patient or delivery does not produce un-acceptable results. In such cases, the method 600 may include reducing the set of accepted parameters by a predefined rule (e.g., negative 0.5 cm margin). In one implementation, the predefined rule may be based on clinical knowledge of radiotherapy and physiological effects of radiation dose in specific organs and tissue types. The predefined rule may be defined by a user using a user interface. In some embodiments, there may be multiple predefined rules, which define geometric and/or dose-volume constraints, and may relate to procedures that can change the parameter values in such constraints (e.g., enable/disable the constraints, or modify the constraints). The rules may be utilized by a processing unit, which is configured to detect a violation of a constraint. If there is a violation, the processing unit may trigger a procedure to change the constraint(s), introduce new constraint(s), or disable constraint(s). Also, in some cases, if the observed variations allow a treatment delivery duty cycle of, for example, 100% (which corresponds with a fast treatment delivery), it may be appropriate to tighten the geometric and/or dosimetric constraints for the treatment. In some embodiments, the tightening of constraints may be performed so that a minimum duty cycle (e.g., 50%) is achieved.

It should be noted that the variations described above may be any variations of geometry of patient anatomy, and/or any variations in the treatment machine geometry in relation to the patient anatomy. The geometric variations imply that there are variations in the dose distribution within the target and organ-at-risk volumes in the patient. The variations may be evaluated and/or represented with geometrical metrics (e.g., distance from original isocenter), and/or dose-volume based metrics using a dose distribution calculated in a patient model.

In some embodiments, the act of determining the one or more limits (item 606) is performed automatically by the delivery limit module.

Also, in some cases, the delivery limit module may be configured to determine the one or more limits during a treatment session. For example, the delivery limit module may determine the limit(s) while treatment energy is being delivered to the patient, or between deliveries of treatment energy during a treatment session (e.g., on the same day).

Figure 7:
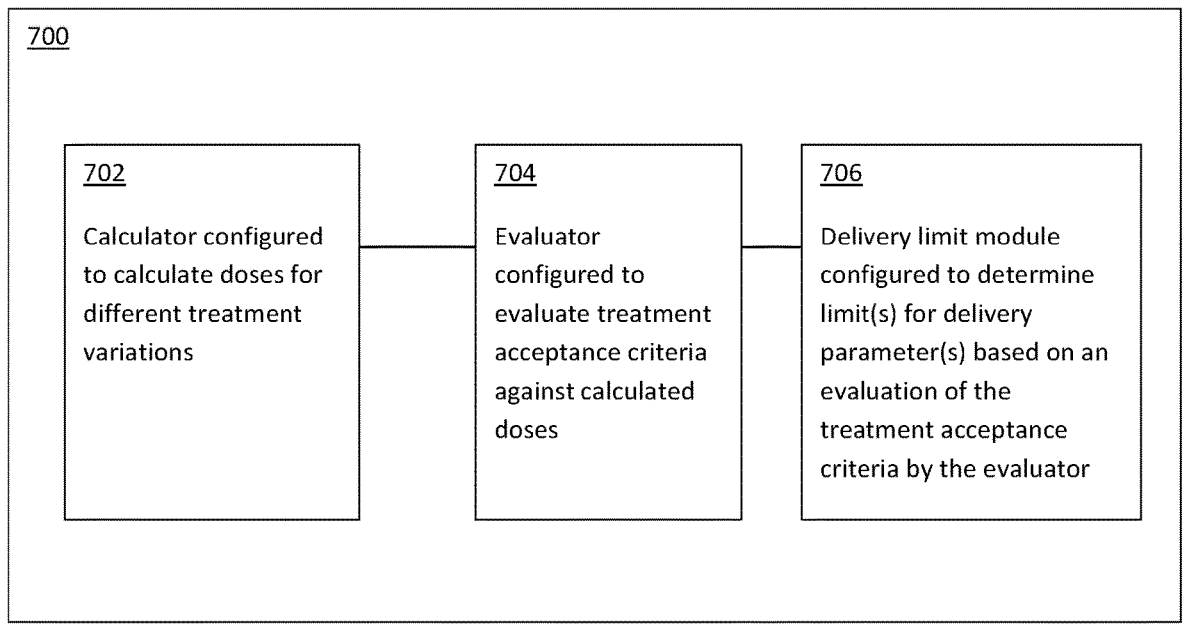
FIG. 7 illustrates an apparatus in accordance with some embodiments.

FIG. 7 illustrates an apparatus 700 that may be used to perform the method 400. The apparatus 700 is for use in a treatment planning process or in a treatment process. The apparatus 700 includes a dose calculator 702 configured to calculate doses for different treatment variations, an evaluator 704 configured to evaluate treatment acceptance criteria against the calculated doses; and a delivery limit module 706 configured to determine one or more limits for one or more delivery parameters based on an evaluation of the treatment acceptance criteria by the evaluator.

By means of non-limiting examples, the delivery parameter may comprise an isocenter position, a leaf position, a gantry angle, a collimator angle, a dose rate, a number of monitoring units, or any combination of the foregoing.

In some cases, the delivery limit module 706 is configured to determine the one or more limits automatically.

Also, in some cases, the delivery limit module 706 may be configured to determine the one or more limits during a treatment session. For example, the delivery limit module 706 may determine the limit(s) while treatment energy is being delivered to the patient, or between deliveries of treatment energy during a treatment session (e.g., on the same day).

In some embodiments, any of the methods 200, 400, 600 may be combined. For example, a method for use in a treatment planning process or in a treatment process may include a combination of the methods 200, 400, a combination of methods 200, 600, a combination of the methods 400, 600, or a combination of the methods 200, 400, 600. Accordingly, an apparatus for use in a treatment planning process or in a treatment process may include a combination of items 302, 304, 502, 504, a combination of items 302, 304, 702, 704, 706, a combination of items 502, 504, 702, 704, 706, or a combination of items 302, 304, 502, 504, 702, 704, 706.

Specialized Processing System

Figure 8:
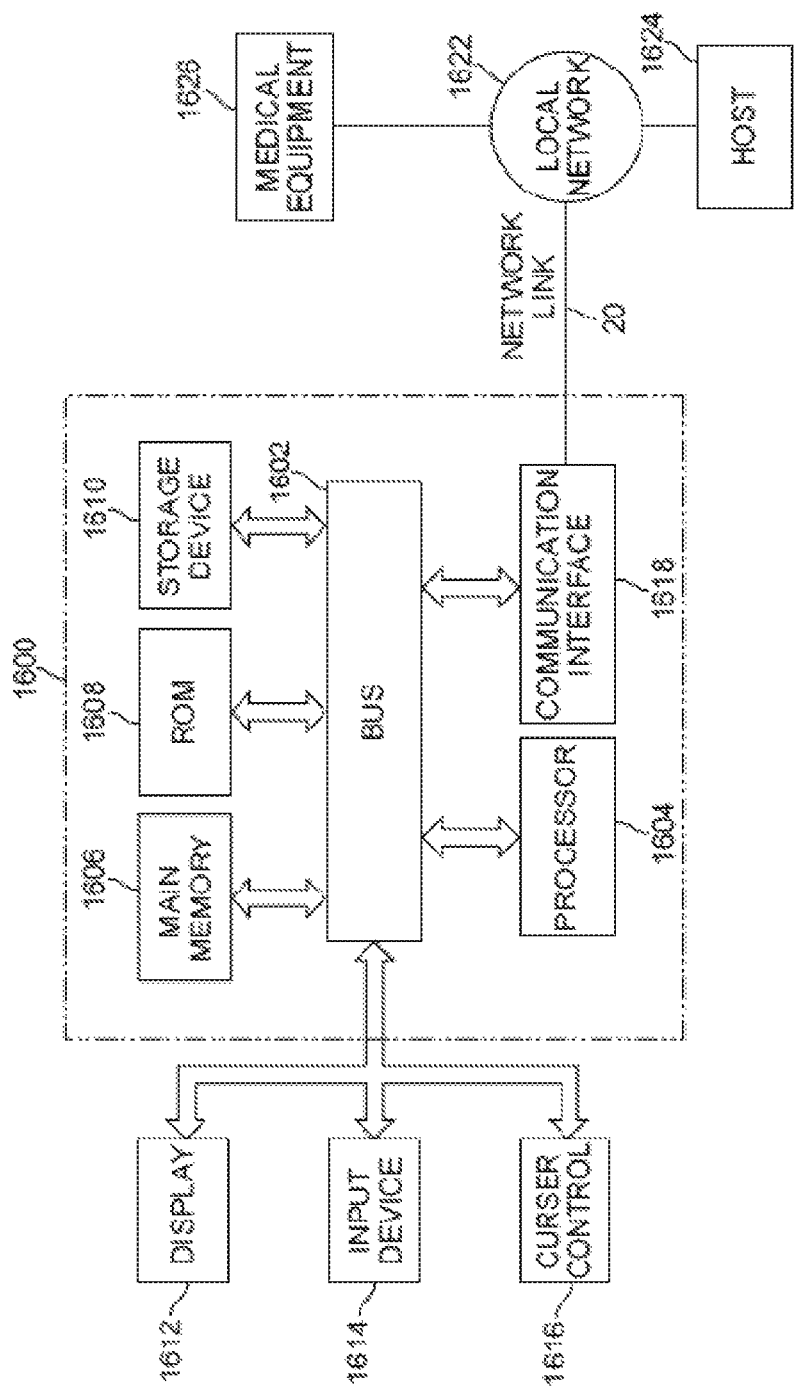
FIG. 8 is a block diagram of a specialized processing system.

FIG. 8 is a block diagram illustrating an embodiment of a specialized processing system 1600 that can be used to implement various embodiments described herein. For example, the processing system 1600 may be configured to implement the method of FIG. 2, 4, or 6, or any combination of the above methods, in accordance with some embodiments. Also, in some embodiments, the processing system 1600 may be used to implement the apparatus of FIG. 3, 5, or 7 and/or the processing unit 54 of FIG. 1. The processing system 1600 may also be used to implement the any or all of the components of the apparatuses 300, 500, 700 described herein. The processing system 1600 may also be an example of any processor described herein.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. An apparatus for use in a treatment planning process or in a treatment process, comprising:
    an input for obtaining a parameter representing a number of beam on-off transitions; and
    a treatment planner configured to determine a treatment plan based on the parameter representing the number of beam on-off transitions;
    wherein the treatment planner is configured to configure a gating window for the treatment plan while considering the number of beam on-off transitions, a duty cycle of treatment, or both, the gating window representing a region wherein a treatment beam is to be delivered when a target in motion passes through the region; and
    wherein the treatment planner is configured to process the parameter representing the number of beam on-off transitions by utilizing the parameter representing the number of beam on-off transitions as an optimization variable in the treatment planning process, and wherein the treatment planner is configured to determine a value of the parameter representing the number of beam on-off transitions, the value of the parameter being equal to the number of beam on-off transitions.

2. The apparatus of claim 1, wherein the beam on-off transitions comprise a transition from beam-on to beam-off, a transition from beam-off to beam-on, or both.

3. The apparatus of claim 1, wherein the treatment planner is configured to optimize the treatment plan to reduce the number of beam on-off transitions.

4. The apparatus of claim 1, wherein the treatment planner is configured to determine the treatment plan during the treatment planning process or during the treatment process.

5. The apparatus of claim 1, wherein the treatment planner comprises a gating window adjustor configured to adjust the gating window.

6. The apparatus of claim 5, wherein the gating window adjustor is configured to adjust the gating window during a treatment session.

7. The apparatus of claim 5, further comprising a motion data analyzer configured to analyze motion data associated with the target, wherein the gating window adjustor is configured to adjust the gating window based on a result from the act of analyzing.

8. The apparatus of claim 5, further comprising a treatment progress monitor configured to determine a status parameter indicating a treatment progress, wherein the gating window adjustor is configured to adjust the gating window based on the status parameter.

9. The apparatus of claim 5, further comprising a treatment duration estimator configured to determine an expected treatment duration based at least in part on a planned monitor unit and the width of the gating window.

10. The apparatus of claim 1, further comprising a delivery limit module configured to determine a limit for a delivery parameter based on a treatment acceptance criterion.

11. The apparatus of claim 10, wherein the delivery parameter comprises an isocenter position, a leaf position, a gantry angle, a collimator angle, a dose rate, a number of monitoring units, or any combination of the foregoing.

12. The apparatus of claim 10, further comprising:
a dose calculator configured to calculate doses for different treatment variations; and
an evaluator configured to evaluate treatment acceptance criteria against the calculated doses, the treatment acceptance criteria including the treatment acceptance criterion;
wherein the delivery limit module is configured to determine the limit for the delivery parameter based on an evaluation of the treatment acceptance criteria by the evaluator.

13. The apparatus of claim 1, wherein the apparatus is configured to configure the gating window by changing a position of the gating window.

14. The apparatus of claim 1, wherein the apparatus is configured to change a width of the gating window.

15. The apparatus of claim 1, wherein the treatment planner is configured to configure the gating window to reduce the number of beam on-off transitions.

16. The apparatus of claim 1, wherein the treatment planner is configured to configure the gating window to increase the duty cycle of treatment.

17. The apparatus of claim 1, wherein the treatment planner is configured to obtain a first priority assigned for the number of beam on-off transitions, and to obtain a second priority assigned for the duty cycle, the second priority being different from the first priority; and
wherein the treatment planner is configured to consider the first priority assigned for the number of beam on-off transitions and the second priority assigned for the duty cycle of treatment, when configuring the gating window.

18. The apparatus of claim 1, wherein the treatment planner is configured to configure the gating window based on both (1) a goal of treatment delivery time and (2) passed treatment delivery time.

19. A method for use in a treatment planning process or in a treatment process, comprising:

obtaining, by an input, a parameter representing a number of beam on-off transitions; and
determining, using a treatment planner, a treatment plan based on the parameter representing the number of beam on-off transitions;
wherein the act of determining the treatment plan, or the method, comprises configuring a gating window for the treatment plan while considering the number of beam on-off transitions, a duty cycle of treatment, or both, the gating window representing a region wherein a treatment beam is to be delivered when a target in motion passes through the region; and
wherein the act of determining the treatment plan also comprises processing, by the treatment planner, the parameter representing the number of beam on-off transitions by utilizing the parameter representing the number of beam on-off transitions as an optimization variable in the treatment planning process, and determining a value of the parameter representing the number of beam on-off transitions, the value of the parameter being equal to the number of beam on-off transitions.

20. The method of claim 19, wherein the beam on-off transitions comprise a transition from beam-on to beam-off, a transition from beam-off to beam-on, or both.

21. The method of claim 19, wherein the act of determining the treatment plan is performed during the treatment planning process or during the treatment process.

22. The method of claim 19, further comprising analyzing motion data associated with the target, wherein the gating window is configured based on a result from the act of analyzing.

23. The method of claim 19, further comprising determining a status parameter indicating a treatment progress, wherein the gating window is configured also based on the status parameter.

24. The method of claim 19, further comprising determining a limit for a delivery parameter based on a treatment acceptance criterion.

25. The method of claim 24, wherein the delivery parameter comprises an isocenter position, a leaf position, a gantry angle, a collimator angle, a dose rate, a number of monitoring units, or any combination of the foregoing.

26. The method of claim 24, further comprising:
calculating doses for different treatment variations; and
evaluating treatment acceptance criteria against the calculated doses, the treatment acceptance criteria including the treatment acceptance criterion;
wherein the limit for the delivery parameter is determined based on a result from the act of evaluating the treatment acceptance criteria.

27. The method of claim 19, wherein the gating window is configured by changing a position of the gating window.

28. The method of claim 19, wherein the gating window is configured by changing a width of the gating window.

29. The method of claim 19, wherein the gating window is configured by the treatment planner to reduce the number of beam on-off transitions.

30. The method of claim 19, wherein the gating window is configured by the treatment planner to increase the duty cycle of treatment.

31. The method of claim 19, wherein the treatment planner performs the act of configuring the gating window while considering respective priorities assigned for the number of beam on-off transitions and the duty cycle of treatment.

32. The method of claim 19, wherein the gating window is configured by the treatment planner based on both (1) a goal of treatment delivery time and (2) passed treatment delivery time.

33. An apparatus for use in a treatment planning process or in a treatment process, comprising:
- an input for obtaining a parameter representing a number of beam on-off transitions; and
- a treatment planner configured to determine a treatment plan based on the parameter representing the number of beam on-off transitions;
- wherein the treatment plan includes a gating window, the gating window representing a region wherein a treatment beam is to be delivered when a target in motion passes through the region represented by the gating window; and
- wherein the treatment planner is also configured to adjust the gating window based on both (1) a goal of treatment delivery time and (2) passed treatment delivery time, wherein the passed treatment delivery time is treatment time that has passed, and includes both previous beam-on time and beam-off time.

* * * * *